United States Patent [19]

Frazier

[11] 4,055,071
[45] Oct. 25, 1977

[54] METHOD AND APPARATUS FOR DETERMINING THE WET STRENGTH OF PAPER

[75] Inventor: William C. Frazier, Vancouver, Canada

[73] Assignee: MacMillan Bloedel Limited, Vancouver, Canada

[21] Appl. No.: 685,160

[22] Filed: May 11, 1976

[51] Int. Cl.$^2$ .................. G01N 3/30; G01N 33/34
[52] U.S. Cl. .................................... 73/12; 73/102
[58] Field of Search ........................ 73/12, 102, 159

[56] References Cited

U.S. PATENT DOCUMENTS

| 1,709,638 | 4/1929 | Thwing | 73/12 |
| 2,264,412 | 12/1941 | Shindel | 73/102 X |
| 2,648,975 | 8/1953 | Eves | 73/102 X |
| 2,748,596 | 6/1956 | Tasker | 73/12 |

OTHER PUBLICATIONS

"Equipment to Measure the Energy Absorption of Films at High Strain Rates" by Spangler et al., Journal of Applied Physics 3-57, pp. 329-333.

Primary Examiner—James J. Gill
Attorney, Agent, or Firm—Fetherstonhaugh & Company

[57] ABSTRACT

An apparatus and method are disclosed for determining the wet strength of paper. It is necessary to know the wet strength of paper in order to determine the runnability of pulp in the papermaking machine. Present devices for measuring the wet strength of paper are slow and complex. The present apparatus includes a means for releasing a ball from a predetermined height to drop freely in a vertical path, clamp means to support a sheet of wet paper and to position the sheet at a pre-determined location within the vertical path of the ball and perpendicular thereto, and means for determining speed of the ball dropping in the vertical path below the clamp means. The method includes steps of releasing a ball from a predetermined height to drop freely in a vertical path, measuring the speed of the ball at a first pre-determined location in the vertical path, positioning a sheet of wet paper in a horizontal plane at a second pre-determined location above the first location in the vertical path, releasing another ball having the same size and mass as the first ball to drop freely in the vertical path and rupture the sheet of wet paper, measuring the speed of the second ball after it has ruptured the sheet of wet paper at the first location in the vertical path and determining the rupture energy of the sheet of wet paper and thus the strength of the wet paper.

12 Claims, 4 Drawing Figures

METHOD AND APPARATUS FOR DETERMINING THE WET STRENGTH OF PAPER

The present invention relates to the wet strength of paper. More specifically, the present invention relates to a method and apparatus for determining the wet strength of a sample paper sheet.

To determine the runnability of pulp in a papermaking machine, it may be necessary to know what the wet strength of the wet paper will be. Sample hand-formed sheets are prepared from chemical or mechanical pulp that is desired to be used in the paper machine. These hand sheets are produced on a device such as a British standard sheet machine and after forming, the sheets are pressed between various numbers of blotters and plates for a predetermined time and at a predetermined pressure to obtain a desired moisture content for testing. These sample hand sheets are tested for wet strength to determine whether the pulp is satisfactory for the production of paper. The wet strength measurement of the pulp presently involves forming strips in a hand sheet machine with a mold, clamping a strip in a testing device between two jaws, one being fixed to a load-sensing cell and the other movable, and then applying tension at a moderately increased rate to the strip until it ruptures. Some testing devices measure both the rupture load and the strain and give information that records the failure history of a wet strip of paper. The present known testing devices are preferably used only in a laboratory and generally require a considerable time for the results of the tests to be obtained.

The present invention provides a novel apparatus for determining the wet strength of paper that uses a complete hand sheet as prepared on a British standard sheet machine or other similar equipment. The hand sheet does not need to be cut into strips, but is clamped between two discs where as many as eight test results may be obtained from one sheet. The apparatus eliminates the intermediate step of strain determination and measures through a horizontally clamped wet hand sheet. It is found that the apparatus is very precise and gives figures which correlate closely with maximum tension or energy to rupture as measured in other types of testing devices, such as those incorporating a wet paper strip clamped between two jaws. Furthermore, the present apparatus reduces the time for obtaining test results over that of other testing devices and enables results to be available within about 10 minutes. This advantage in time saving is particularly important when the start-up of a production run on a paper machine depends on the test results.

The present invention provides an apparatus for determining the wet strength of paper comprising means for releasing a ball from a predetermined height to drop freely in a vertical path, clamp means to support a sheet of wet paper and to position the sheet at a predetermined location within the vertical path of the ball and perpendicular thereto, and means for determining speed of the ball dropping in the vertical path below the clamp means.

There is also provided in the present invention a method of determining the wet strength of paper comprising the steps of releasing a first ball from a predetermined height to drop freely in a vertical path, measuring the speed of the first ball at a first predetermined location in the vertical path, positioning a sheet of wet paper in a horizontal plane at a second predetermined location above the first location in the vertical path, releasing a second ball having the same size and mass as the first ball, to drop freely in the vertical path and rupture the sheet of wet paper, measuring the speed of the second ball after it has ruptured the sheet of wet paper at the first location in the vertical path, determining the rupture energy of the sheet of wet paper from the difference in speeds between the first ball and the second ball.

In drawings which illustrate embodiments of the invention:

Figure 1:
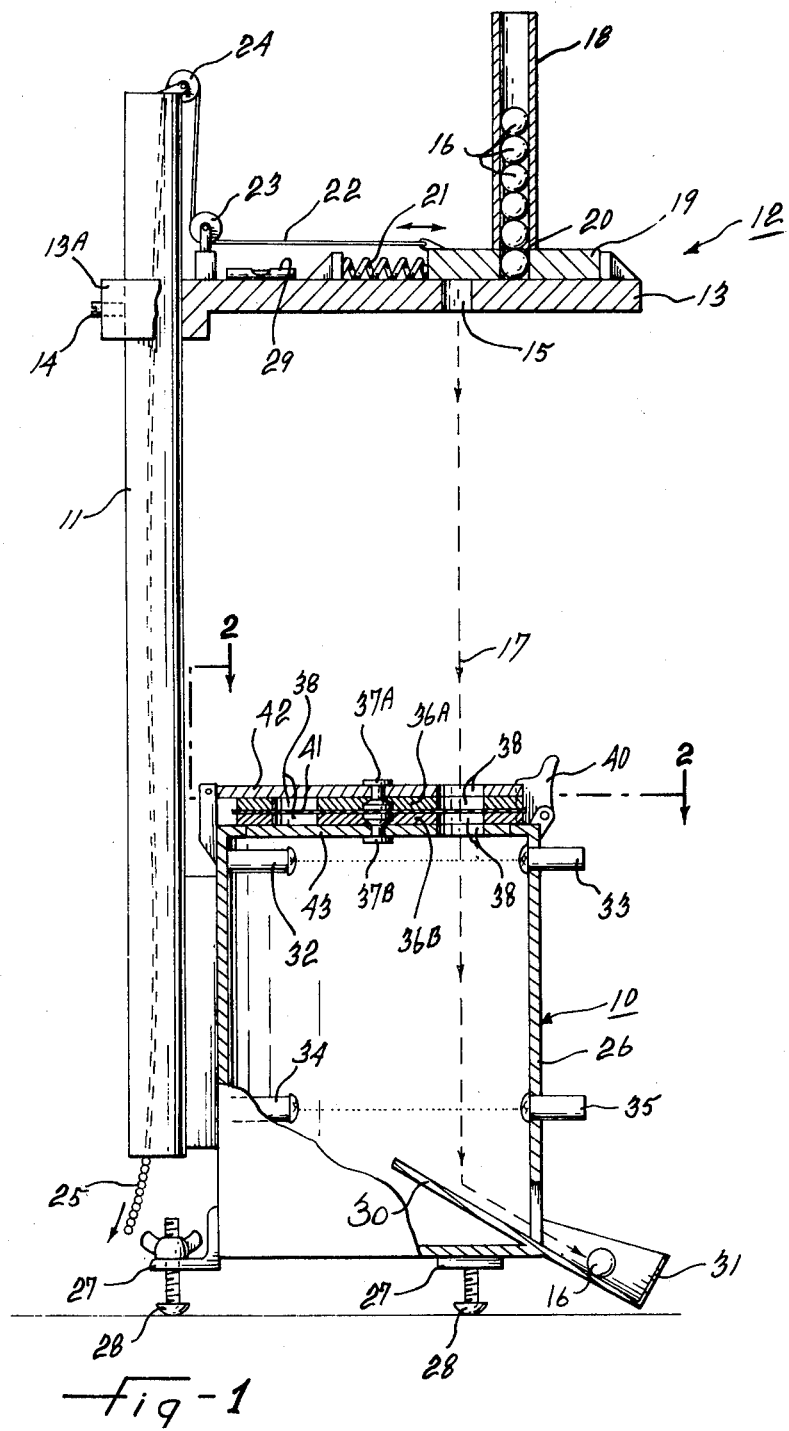
FIG. 1 is a sectional elevation of one embodiment of the apparatus of the present invention.

Referring now to FIG. 1, the apparatus comprises three main components: a base 10, a column 11 attached to one side of the base 10, and a dropping mechanism 12 slidably mounted on the column 11. The dropping mechanism 12 has a cross arm 13 which extends horizontally from the column 11. One end of the cross arm 12 has a collar 13A which slides up and down the column. The cross arm 13 is positively located by a set screw 14 clamping the collar 13A to the column 11. In another embodiment, the cross arm is not slidable on the column but is fixed. This provides a fixed height for the dropping mechanism. The cross arm 13 has a ball dropping hole 15 in the approximate centre thereof which allows a ball 16 to freely fall in a vertical path 17. On the upper surface of the cross arm 13 a columnar magazine 18 holds a plurality of balls 16, all of the same size and mass. The balls 16 are preferably made from steel with a polished surface such as the type used in ball bearings. The magazine 18 is placed externally of the dropping hole 15 and a sliding plate 19 with a ball orifice 20 therein transfers a ball 16 from the magazine 18 to the dropping hole 15. A compression spring 21 returns the sliding plate 19 to a position with the ball orifice 20 aligned under the magazine 18 allowing another ball 16 to fall into the orifice 20. A string or cord 22 is attached to the sliding plate 19 and passes under a pulley 23 attached to the collar 13A of the cross arm 13. The cord 22 extends upwards passing over a second pulley 24 attached at the top of the column 11 and then down through the column terminating in a chain 25. A pull on the chain 25 moves the sliding plate 19, thus moving a ball 16 from the magazine 18 to the dropping hole 15 and providing manual operation for a ball 16 to drop down the vertical path 17.

The base 10 has a cylindrical casing 26 with three feet 27 attached around the periphery of the casing 26 and having levelling screws 28 as legs to level the apparatus. A bubble level indicator 29 is located on the cross arm 13 to show when the apparatus is level. A ball ramp 30 is provided at the bottom of the casing 26, positioned under the vertical path 17 and directs the balls 16 to a collecting tray 31. An upper photocell 32 is mounted on the inside wall in the upper portion of the casing 26, and an upper light 33 is positioned in the same horizontal plane as the upper photocell 32 with a straight line between the upper light 33 and the upper photocell 32 passing through the vertical path 17. A lower photocell 34 is mounted on the inside wall of the casing directly below and at a predetermined distance from the upper photocell 32. A lower light 35 is positioned in the same horizontal plane as the lower photocell 34 with a straight line between the lower light 35 and the lower photocell 34 passing through the vertical path 17. Thus when a ball 16 falls freely in the vertical path 17 it first cuts off the light source to the upper photocell 32, and then cuts off the light source to the lower photocell 34. The time between these two steps can be used to determine the speed of the ball 16.

Figure 2:
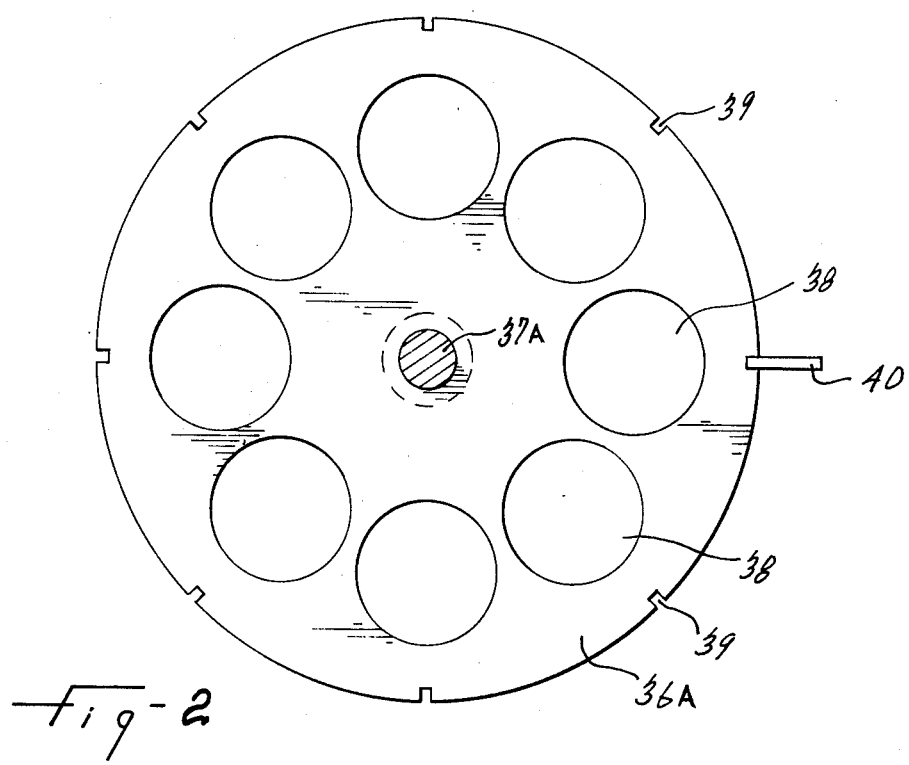
FIG. 2 is a plan view of the clamping disc taken at line 2—2 of FIG. 1.

The hand sheet carrier consists of a pair of rotating discs 36A, 36B as shown in FIG. 2. The upper disc 36A has a central bushing 37A representing the axis of rotation and eight similar sized round apertures 38 equi-spaced from and about the axis of rotation. The lower disc 36B also has a central bushing 37B and eight apertures 38 the same size and in line with the upper disc 36A. Each of the apertures 38 is larger in diameter than the diameter of a ball 16. A slot 39 is located at the periphery of the upper disc 36A and the lower disc 36B in line with the axis of rotation and the centre of each aperture 38. A locking plate 40 pivoted to the outside of the casing 26 is spring-loaded to fit and lock into the slot 39 and hold an aperture 38 in the correct position directly in line with the vertical path 17. After a ball 16 has been dropped, the locking plate 40 is moved out of the slot 39, and the pair of discs 36A, 36B are rotated to the next aperture 38 where the locking plate 40 engages the next slot 39. The upper disc 36A is attached to a hinged top plate 42 at the central bushing 37A so that it can be raised exposing the lower disc 36B attached to a fixed bottom plate 43 at the central bushing 37B. The upper disc 36A and top plate 42 are raised and a wet hand sheet 41 is placed on the lower disc 36B. The upper disc 36A and top plate 42 are then lowered on to the sheet 41 clamping it in place by the weight of the disc and plate. The upper disc 36A, wet sheet 41 and lower disc 36B can rotate as a unit when the locking plate 40 is pivoted to the outside. The top plate 42 and the bottom plate 43 both have an aperture 38 in the vertical path 17 for the passage of a ball 16.

Figure 3:
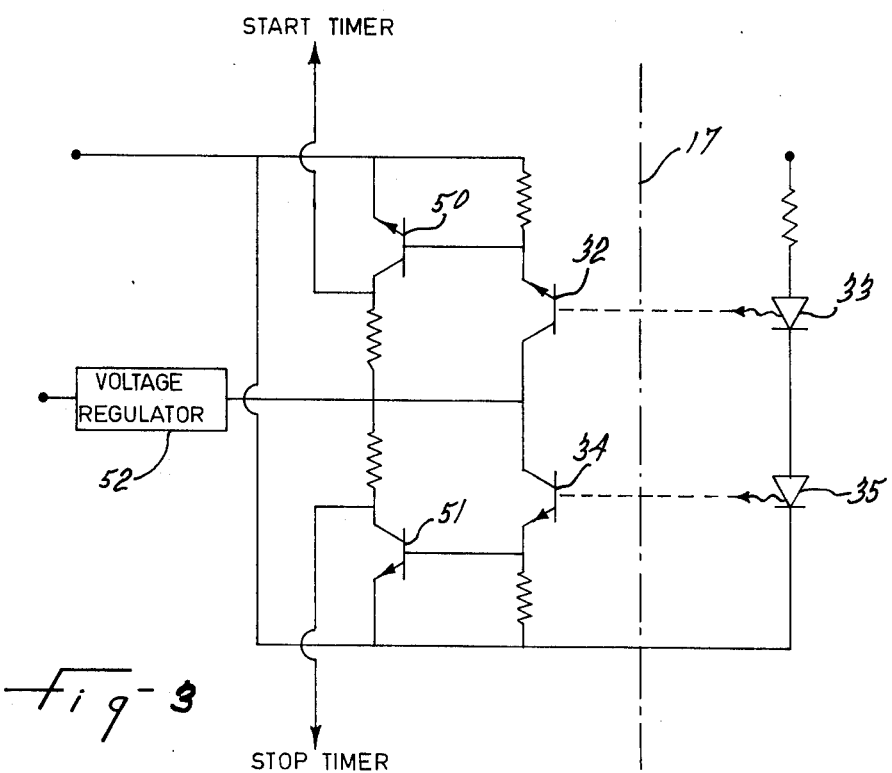
FIG. 3 is a wiring diagram for one embodiment of the present invention.

In one embodiment, the upper light 33 and the lower light 35 are infrared-emitting diodes and the upper photocell 32 and the lower photocell 34 are phototransistors specifically sensitive to the infrared spectrum. By using the infrared spectrum the spurious readings from light reflections off the ball surfaces are eliminated. As may be seen in FIG. 3, beams of infrared energy from the emitting diodes 33 and 35 fall on the phototransistors 32, 34 representing the upper and lower photocells and pass a current to hold each collector of the transistors 50, 51 at ground potential. When a beam is broken by a falling ball, the base of the phototransistor 32 or 34 is unloaded allowing a sharply rising signal to appear at the particular collector which starts or stops a timer (not shown) which is compatible with the circuit for the photocells. The circuit has a voltage regulator 52 and is able to detect a time difference of several microseconds which is three to four orders of magnitude smaller than the ball drop times ensuring very great accuracy. In one embodiment the timer is a solid state portable instrument, accurate to ±10 microseconds.

To use the apparatus, an operator first pulls the chain 25 so that the slide 19 moves along the cross arm 13, thus causing a ball 16 to drop through the dropping hole 15 and fall along the vertical path 17. In the first instance the sheet carrier is empty and as the ball 16 passes the upper light 33, it interrupts the beam to the upper photocell 32 and starts the timer. The ball 16 then interrupts the beam from the lower light 35 to the lower photocell 34 and this stops the timer. The ball 16 then lands on the ball ramp 30 and rolls down to the collecting tray 31. The magazine 18 holds at least eight balls 16 and a full magazine of balls is preferably dropped before a sheet is inserted between the discs of the sheet carrier. The timer results for the drops are compared and if the coefficient of variation for the tests is greater than 0.5%, the apparatus should be checked for malfunction before continuing.

Hand sheets of paper having the desired basis weight are produced on the British standard sheet machine in the usual manner. In one embodiment sheets are individually couched off and pressed between various numbers of blotters and plates for five minutes at 50 lbs. per square inch pressure in a British standard press to obtain the desired moisture contents for testing. Preparation of these sheets does not form part of the present invention but is well known in the art and each operator of wet strength testing devices establishes his own moisture levels for the particular pulp and the particular manner in which the sheet is formed dependent on the type of paper to be produced on a paper machine. Wet sheets are generally kept in their blotters and plate stacks in polyethylene bags until just prior to use. A sheet 41 is taken from the stack and placed on the lower disc 36B. The upper disc 36A and top plate 42 are then placed on the lower disc sandwiching the sheet. The pair of discs 36A, 36B are aligned so an aperture 38 on both discs is in the vertical path 17, thus allowing a ball 16 to be dropped down the vertical path 17 and strike only the sheet 41. The locking plate 40 locks into a slot 39 in the pair of discs 36 so one aperture is positioned in the vertical path 17. A first ball is then dropped to rupture the particular portion of sheet 41 that appears in the aperture 38. The distance between the underside of the cross arm 13 and the beam between the upper light 33 and the upper photocell 32 remains constant for the drops with and without the hand sheets 41. The timer records the time for the ball 16 to fall from the upper photocell 32 to the lower photocell 34. After the drop, the pair of discs 36 are rotated by releasing the locking plate 40 from the slot 39 and turning the discs 36 to the next position. Another ball is dropped and the time recorded. Thus eight tests are carried out on one hand sheet. The hand sheet is then weighed, dryed and weighed again to determine moisture content. Another hand sheet is then taken from the stack and tested in the same manner. At the end of the testing of a number of hand sheets, a magazine of balls is dropped without any sheet being present to ensure that the stability of the apparatus has been maintained throughout the tests.

The energy of a ball in free fall is then determined from the formula $E = (M/2)[(H/T) - (GT/2)]^2$ where E is the energy, M is the mass of the ball, H is the distance between the upper photocell 32 and the lower photocell 34, G is the acceleration due to gravity, and T is an average time for the ball to traverse the distance H taken from the eight drops. The times of the eight tests for each hand sheet are averaged and a standard deviation calculated. Using the same formula as free fall, the energy for a ball rupturing a hand sheet is determined. The energy to rupture a sheet, referred to as the rupture energy, is then determined by subtracting the energy of a ball after rupturing a sheet from the energy of a ball in free fall. The rupture energy of each sheet is compared with the moisture content, as moisture content affects the strength of pulp sheets. By correlation the wet strength of a hand sheet may then be determined.

In testing the apparatus it was found that very small scatter was associated with the series of drops for the free-fall data. Thus the accuracy of the machine is satisfactory. Furthermore, the precise control of basis weight and moisture content of the paper hand sheets yield proportionately more accurate results than other types of testing devices, in particular, the Pearson-Kelk wet tensile tester. It was found the actual wet rupture energy of the sheet ranges from 20-50% of the total energy of the ball. Any increase beyond 50% resulted in excessive deflection of the ball by the sheet causing erroneous readings. It was observed in the tests that with a ½ inch diameter ball, pieces of web sheet about ¼ inch in diameter sometimes broke away from the sheet and held to the ball. This additional portion of paper increased the mass of the ball. Thus slight errors occurred in the energy figures. In practice it was found that these errors caused a change of up to 2% from the actual basic energy values. Furthermore, it was also found that these small pieces of paper carried away by the ball often collected inside the casing 26 and from time to time had to be blown out.

Figure 4:
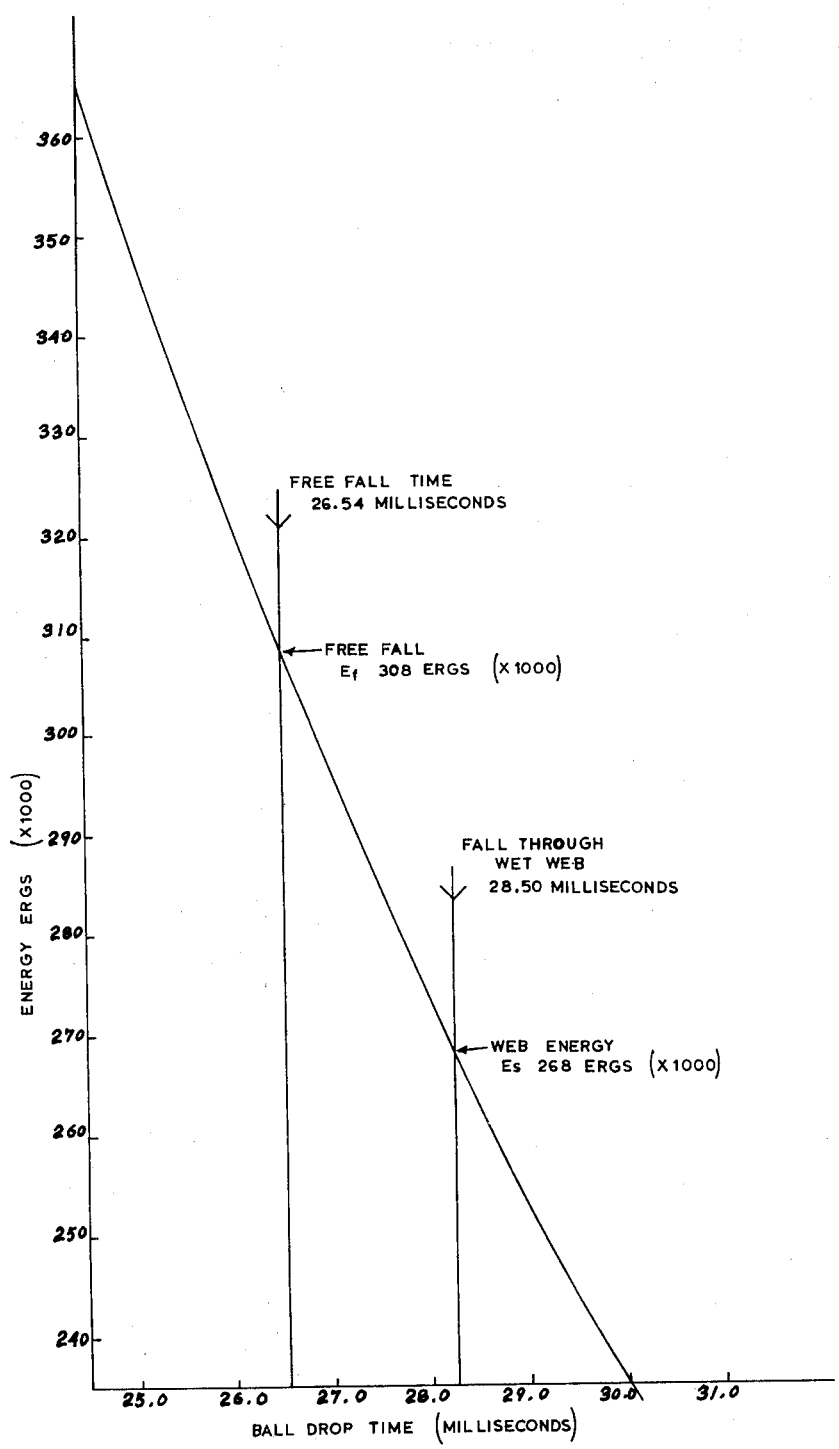
FIG. 4 is a graph of a ball drop time against energy.

In one series of tests, steel balls ½ inch in diameter and all of the same magnitude were used. The distance for the drop from the underside of the cross arm to the wet hand sheet was 15 inches. A 3 inch distance existed between the upper and lower photocells which was the distance of fall timed by the timer. Results of the tests were averaged and plotted on the graph shown in FIG. 4. The average free fall time was 26.54 milliseconds and the average time through the wet web was 28.54 milliseconds. The resultant rupture energy value of the wet web was 308 - 268 = 40 ergs ($\times$ 1000).

The height of the cross arm above the hand sheet, and hence the upper photocell, may be varied by releasing the set screw and moving it up and down as desired. The drop distance is sufficient to ensure that the ball passes through the wet sheet without being deflected by the rupture. Before commencing tests, the apparatus is levelled and this is achieved by adjustment to the level screws 28 so that the bubble unit 29 is centred.

The embodiments of the invention in which an exclusive property or privilege is claimed are defined as follows:

1. An apparatus for determining the wet strength of paper comprising means for releasing a ball from a predetermined height to drop freely in a vertical path, clamp means to support a sheet of wet paper and to position the sheet at a predetermined location within the vertical path of the ball and perpendicular thereto, wherein the clamp means includes two discs clamped together to hold a sheet of wet paper therebetween, the two discs having a central axis of rotation, each of the two discs having a plurality of similar sized apertures equi-spaced from and about the axis of rotation, such that the apertures of one disc line up with the apertures in the other disc, wherein the wet paper is positionable between the discs so as to obstruct the apertures, the two discs being rotatably mounted about the axis of rotation such that each of the apertures is positively locatable in the vertical path of the ball, and means for determining speed of the ball dropping in the vertical path below the clamp means.

2. The apparatus according to claim 1 wherein the means for releasing a ball includes a magazine for storing a plurality of balls of similar size and mass and a manually operated feeder to transfer a ball from the magazine to a release position in the vertical path.

3. The apparatus according to claim 1 wherein the means for determining the speed of the ball includes an upper and lower photocell a predetermined vertical distance apart adjacent the vertical path, an upper light source on the same horizontal plane as the upper photocell, and on the opposite side of the vertical path, a lower light source on the same horizontal plane as the lower photocell and on the opposite side of the vertical path, and a timer adapted to determine a time interval from an interruption of light to the upper photocell to an interruption of light to the lower photocell caused by the ball dropping in the vertical path.

4. The apparatus according to claim 3 wherein the upper light source and the lower light source transmit infrared energy, and the upper photocell and the lower photocell are only sensitive to infrared energy.

5. The apparatus according to claim 3 wherein the timer is capable of ±10 microsecond accuracy.

6. The apparatus according to claim 1 including a level indicator adjacent the means for releasing a ball and levelling means to level the apparatus.

7. The apparatus according to claim 1 including a height adjusting means for changing the predetermined height of the means for releasing the ball.

8. A method of determining the wet strength of paper with an apparatus comprising means for releasing a ball, from a predetermined height to drop freely in a vertical path, clamp means to support a sheet of wet paper and to position the sheet at a predetermined location within the vertical path of the ball and perpendicular thereto, wherein the clamp means includes two discs clamped together to hold a sheet of wet paper therebetween, the two discs having a central axis of rotation, each of the two discs having a plurality of similar sized apertures equi-spaced from and about the axis of rotation, such that the apertures of one disc line up with the apertures in the other disc, wherein the wet paper is positionable between the discs so as to obstruct the apertures, the two discs being rotatably mounted about the axis of rotation such that each of the apertures is positively locatable in the vertical path of the ball, and means for determining speed of the ball dropping in the vertical path below the clamp means, the method comprising the steps of releasing a first ball from a predetermined height to drop freely in a vertical path, aligned with one of the apertures of the clamp means, measuring the speed of the first ball at a predetermined measurement location in the vertical path, positioning the sheet of wet paper in the clamp means in a horizontal plane, the predetermined location of the clamp means being above the measurement location in the vertical path, releasing a second ball having the same size and mass as the first ball, to drop freely in the vertical path and rupture a portion of the sheet of wet paper obstructing one of the apertures, measuring the speed of the second ball after it has ruptured the sheet of wet paper at the measurement location in the vertical path, determining the rupture energy of the sheet of wet paper from the difference in speed between the first ball and the second ball, rotating the clamp means to bring each of the apertures in seriatim into the vertical path and releasing additional balls in seriatim to drop freely in the vertical path and rupture the wet paper obstructing the apertures, measuring the speed of each additional ball after it has ruptured the wet paper obstructing each aperture, determining the rupture energy of the wet paper from the difference in speed between the first ball and each additional ball dropped in seriatim.

9. The method according to claim 8 wherein the steps of releasing the first ball and measuring the speed of the first ball are carried out initially to calibrate an apparatus for determining the rupture energy for a plurality of sheets of wet paper.

10. The method according to claim 8 wherein the speed of the balls dropping freely in the vertical path is determined from the time interval for a falling ball to interrupt a horizontal upper light beam and a horizontal lower light beam a predetermined distance apart in the vertical path.

11. The method according to claim 8 wherein eight balls are released without positioning a sheet of wet paper, and a further eight balls are released to rupture a sheet of wet paper at eight different positions in the same horizontal plane, and the average speeds are employed to determine the rupture energy of the sheet of wet paper.

12. The method according to claim 8 including the steps of weighing the sheet of wet paper after being ruptured by the second ball, drying the sheet, and weighing the sheet again to determine moisture content of the sheet.

* * * * *